United States Patent [19]

Stevens et al.

[11] Patent Number: 5,924,583
[45] Date of Patent: *Jul. 20, 1999

[54] TISSUE CULTURE FLASK

[75] Inventors: Timothy A. Stevens, Madison; Edward Mussi, Hewitt, both of N.J.

[73] Assignee: Becton Dickinson and Company, Franklin Lakes, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/859,019

[22] Filed: May 20, 1997

Related U.S. Application Data

[63] Continuation of application No. 08/444,332, May 18, 1995, abandoned.

[51] Int. Cl.[6] ................................................ B65D 1/02
[52] U.S. Cl. .......................... 215/40; 206/503; 215/44; 215/380; 435/304.1
[58] Field of Search ................................. 215/40–44, 10, 215/11.1, 380, DIG. 3, 371–376, 382; 435/304.1, 304.2, 304.3, 298.1, 298.2; 206/508, 503; 220/571, 608, DIG. 6, 605, 606

[56] References Cited

U.S. PATENT DOCUMENTS

| | | | |
|---|---|---|---|
| D. 249,076 | 8/1978 | Meeker et al. | 215/40 X |
| 2,779,472 | 1/1957 | Febbraro | 215/374 X |
| 2,905,351 | 9/1959 | Lerner | 220/605 X |
| 2,947,116 | 8/1960 | Earle et al. . | |
| 3,449,210 | 6/1969 | Rohde . | |
| 3,870,602 | 3/1975 | Froman et al. . | |
| 4,334,028 | 6/1982 | Carver . | |
| 4,676,387 | 6/1987 | Stephenson et al. | 215/11.1 |
| 4,770,854 | 9/1988 | Lyman . | |
| 4,851,351 | 7/1989 | Akamine | 435/304.3 |
| 4,927,764 | 5/1990 | Lyman et al. . | |
| 4,935,371 | 6/1990 | Rickloff | 422/102 X |
| 5,112,957 | 5/1992 | Pollard | 435/304.3 X |
| 5,139,952 | 8/1992 | Honda et al. . | |
| 5,262,326 | 11/1993 | Jaeger et al. | 435/304.3 X |
| 5,272,084 | 12/1993 | O'Connell et al. | 215/DIG. 3 X |
| 5,344,036 | 9/1994 | Stanescu et al. | 215/376 X |
| 5,391,496 | 2/1995 | Kayal et al. | 435/304.3 X |
| 5,482,854 | 1/1996 | O'Leary et al. | 435/304.1 X |
| 5,783,440 | 7/1998 | Stevens | 435/304.1 X |

FOREIGN PATENT DOCUMENTS 60-70067  4/1985  Japan .

Primary Examiner—Stephen K. Cronin
Assistant Examiner—Robin A. Hylton
Attorney, Agent, or Firm—Bruce S. Weintraub; Nanette S. Thomas

[57] ABSTRACT

A laboratory flask is designed for the growth of tissue, cells or microorganisms in a culture medium. The flask includes a bottom wall which accommodates the culture medium. The interior of the flask is accessible from an opening in a side wall through a neck extending outwardly therefrom. The neck of the flask is raised above an upper planar surface of the flask, so as to maximize the height between the neck and the bottom wall, thereby permitting an increase in the usable volume of the flask. The inner wall surface of the neck includes a depending filler wall extending between the inner wall of the neck and the upper planar surface of the flask to fill a gap which would otherwise exist therebetween. The flask permits accommodation of a standard screw-threaded cap to close the neck.

1 Claim, 8 Drawing Sheets

TISSUE CULTURE FLASK

This is a continuation of application Ser. No. 08/444,332, filed on May 18, 1995, now abandoned.

FIELD OF THE INVENTION

The present invention relates generally to laboratory flasks. More particularly the present invention relates to improvements in flasks for growing cells, microorganisms and tissue in a culture medium.

BACKGROUND OF THE INVENTION

Tissue culture flasks are widely used in the laboratory for many purposes. Typically, these flasks are used to culture microorganisms or tissues in a culture medium or agar which is adhered to an interior surface of the flask. The tissues are introduced into the flask through a capped opening. The flask is re-capped and inserted into a stacking facility or chamber, such as an oven, to facilitate the growth of the microorganisms in the medium. In laboratory practice, it is quite common to arrange or stack several tissue culture flasks in a single chamber. Thus, the size of the individual flasks becomes a concern as it desirable to position as many flasks as possible in a single chamber.

Another concern in constructing tissue culture flasks is the volume within the flask which is available for accommodation of both the culture medium as well as the tissue. In order to enhance stackability of the flasks in the chamber, many tissue culture flasks are generally flat rectangular containers having a neck or opening at one end wall permitting access to the interior of the flask. The culture medium is adhered to the bottom wall of the flask. The flask may be filled with culture medium and tissue to a level approaching the bottom of the neck or opening. Thus, the usable volume of the flask is determined by the vertical distance between the bottom wall of the flask and the flask opening, since the culture medium and tissue cannot extend above the flask opening. While spacing the opening from the bottom all of the flask will increase the usable volume of the flask, it does increase the overall size (stacked height) of the flask. This reduces the number of flasks which can be stacked in a chamber. Attempts to decrease the size of the opening, in order to increase the usable volume, result in limiting accessibility to the entire bottom wall of the flask as such access is gained through the opening. Often, in certain situations, it becomes necessary to access the tissue growing in the medium on the bottom wall of the flask. It is desirable for the user to access the entire bottom surface of the flask, including the corners, with a scraper, pipette, or other instrument. Decreasing the size of the opening severely restricts the area of the bottom wall which may be accessed therethrough.

It is therefore desirable to provide a tissue culture flask having a sufficiently large opening so as to permit access to the entire bottom surface thereof without decreasing the usable volume or increasing the stacked height of the flask.

SUMMARY OF THE INVENTION

It is an object of the present invention to provide an improved laboratory flask for the culturing of microorganisms, cells and tissues.

It is a further object of the present invention to provide a tissue culture flask which permits access to the interior of the flask through an opening therein.

It is a still further object of the present invention to provide a tissue culture flask of minimal stacked height which maximizes the usable volume for culture medium and tissue.

The present invention provides a laboratory flask including a flask body having a generally flat bottom wall, upwardly extending front, back, and lateral walls bounding the bottom wall, and an upper, generally planar cover surface which is parallel to the bottom wall to enclose the flask body and define a flask interior. The front wall of the flask body includes a generally circular opening which provide access to the flask interior. An elongate hollow annular neck extends outwardly from the front wall opening and has uniform inner and outer cylindrical walls. A portion of the inner cylindrical wall of the annular neck is positioned above a portion of the planar cover surface. The neck further includes a depending filler wall extending from the inner cylindrical wall. The filler wall fills the gap which would otherwise exist between the inner cylindrical wall of the neck and the portion of the planar cover surface of the flask body.

As more particularly shown by way of the preferred embodiment herein, the bottom wall of the flask includes a upwardly extending ramp surface between the front wall and a main planar portion of the bottom wall. The ramp surface serves to maintain culture medium and tissues on the main portion of the bottom wall. The ramp surface may be transversely concave with respect to the interior of the flask to assure that culture medium and tissue is returned centrally to the bottom wall of the flask. In addition, the back wall of the flask is outwardly bowed, forming a central trough to provide a low collection point so that the entire contents of the flask can be removed with a pipette or other removal instrument.

DETAILED DESCRIPTION OF THE PREFERRED EMBODIMENTS

Figure 1:
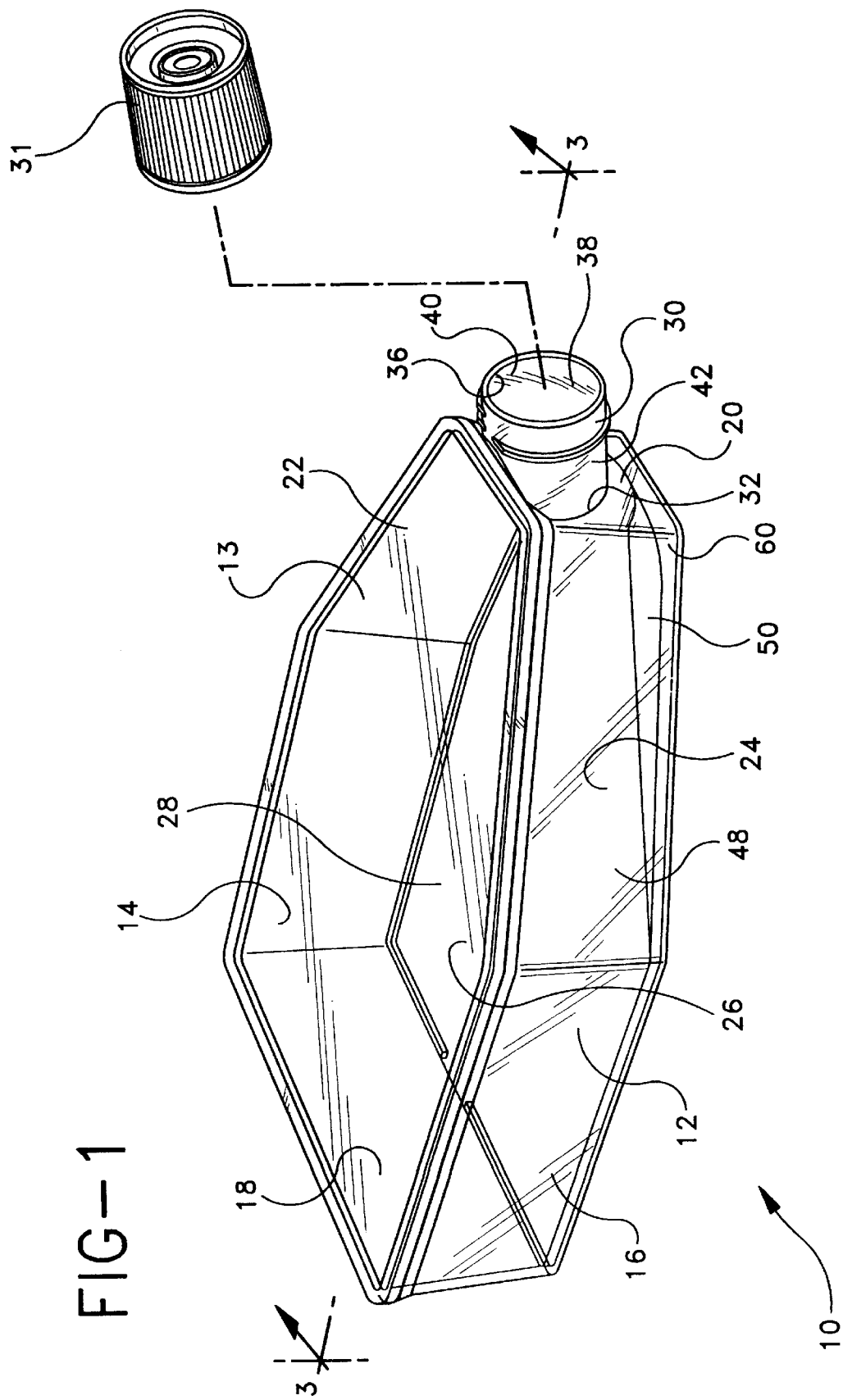
FIG. 1 is a top perspective showing of tissue culture flask of the present invention.

Referring to the drawings, the present invention provides an improved tissue culture flask 10 which permits full access to the interior thereof without a reduction in the usable volume of the flask.

Referring specifically to FIG. 1, flask 10 of the present invention is a generally hexagonally shaped container which may be formed of any suitable material such as a molded transparent plastic, preferably polystyrene. Flask 10 includes a bottom planar wall 12 which is perimetrically bounded by a plurality of upstanding side walls 13. Side walls 13 include a pair of spaced apart elongate generally parallel rear walls 14 and 16 which are spanned by a transverse back wall 18. A front wall 20 extends parallel to back wall 18 and has a transverse extent which is less than the transverse extent of back wall 18. The side walls 13 further include a pair of spaced apart forward transitional walls 22 and 24 extending angularly from rear walls 14 and 16, respectively. Forward transition walls 22 and 24 extend to front wall 20 so that the side walls 13 fully perimetrically bound bottom wall 12.

The side walls 13 extend upwardly to a uniform height defining a planar open surface which is generally parallel to bottom wall 12. A planar cover 26 is positioned over the upper extents of the side walls 13 to enclose flask 10 and to define a bounded interior 28 of flask 10. In the present illustrative embodiment cover 26 is a separable planar member which may be positioned over the upper extents of the side walls. The cover 26 may be permanently bonded in non-removable fashion to the side walls 13 by any well-known bonding technique, such as, for example, ultrasonic welding. It is further contemplated that the flask 10 of the present invention may be constructed with cover 26 being formed as integral part thereof.

The particular shape of the flask 10 of the present invention including the provision and position of forward transition walls 22 and 24 eliminates "blind" corners that would exist in constructing a flask of a more conventional rectangular configuration. Thus, as is well known in the flask art, such configuration of flask 10 permits better access to the interior 28 of the flask with a pipette or other laboratory instrument (not shown).

In order to permit such access to the interior 28 of flask 10, front wall 20 includes an extending neck 30 integrally formed therewith. Neck 30 is generally a uniformly cylindrical member having a first end 32 supported on front wall 20 about a generally circular opening 34 (FIG. 5) formed therein. Neck 30 includes an open second end 36 opposite first end 32 and defines a central bore or passage 38 between the ends and in communication with the interior 28 of flask 10 through opening 34. Central bore 38 is defined by an interior cylindrical wall surface 40 of neck 30. Neck 30 also includes an outer wall surface 42, which in the preferred embodiment is externally screw-threaded so as to accommodate a conventional, internally threaded screw cap 31 for closing bore 38 and sealing the interior 28 of flask 10.

Figure 2:
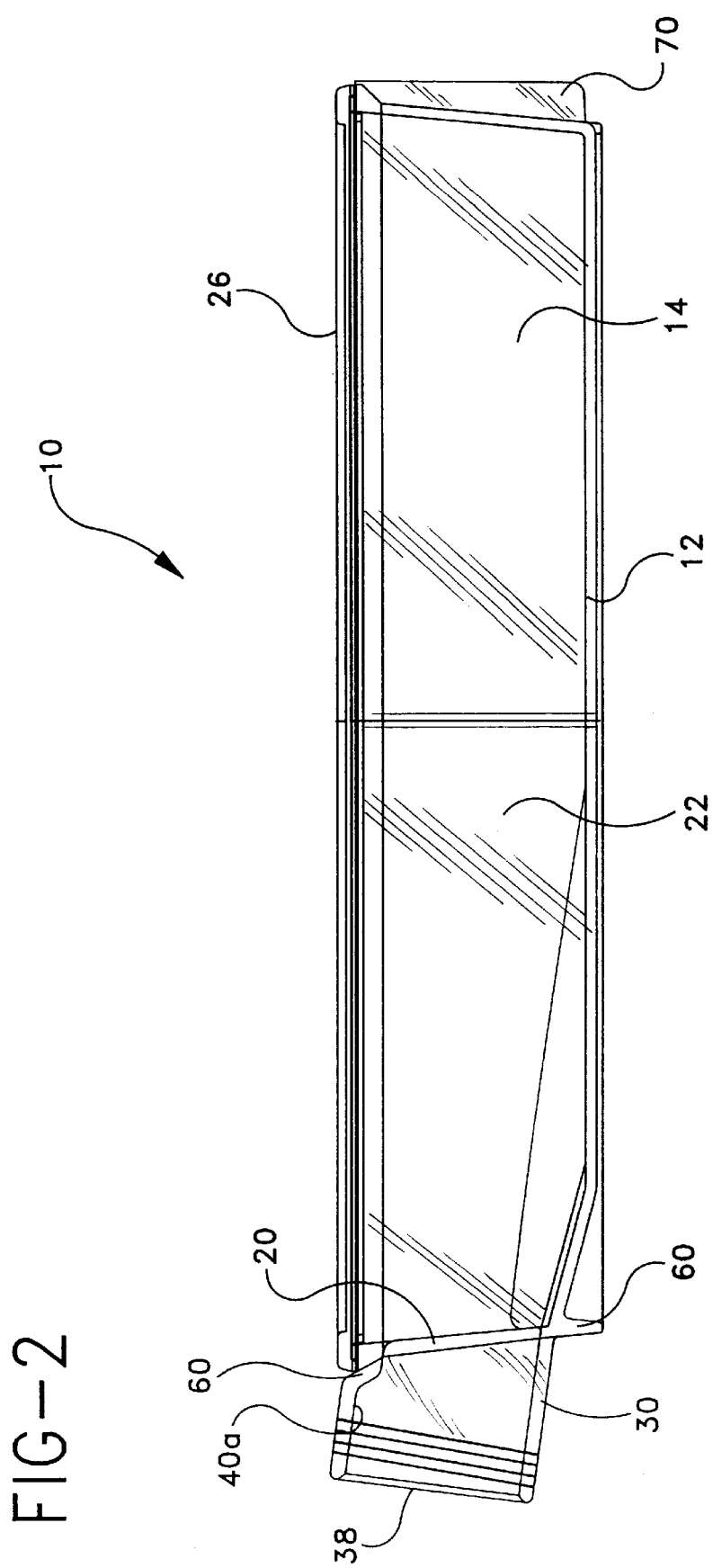
FIG. 2 is a side elevational showing of the tissue culture flask of FIG. 1.
Figure 3:
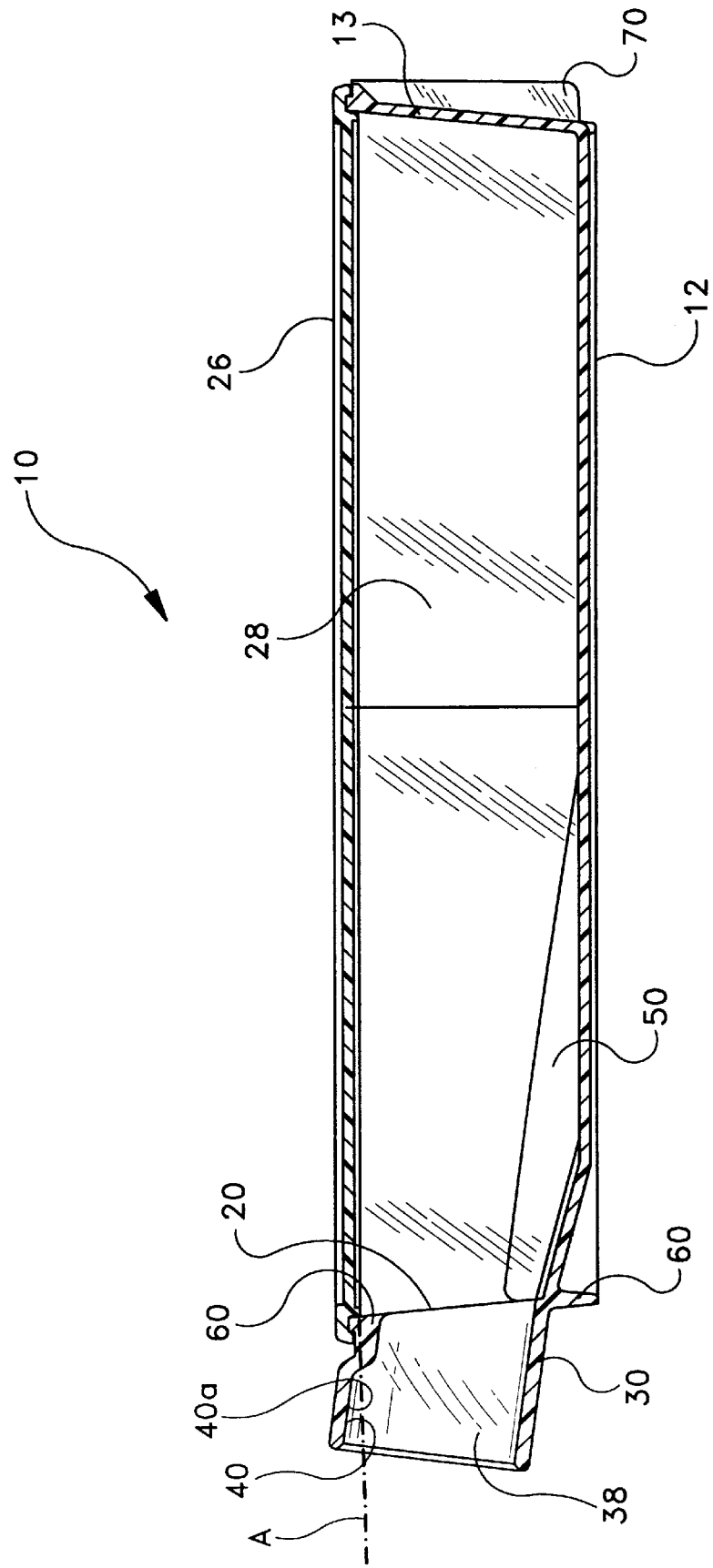
FIG. 3 is a longitudinal cross-section of the tissue culture flask of FIG. 1 taken through line 3–3 thereof.

As shown, particularly in FIGS. 2 and 3, neck 30 is disposed at an upwardly inclined angle with respect to the main plane of bottom wall 12. The upward inclination of neck 30 may be between 5° and 20°, preferably about 7.50° The upwardly inclined angle of neck 30 serves two advantageous purposes. First, it facilitates access to the bottom wall 12 with a pipette or other instrument inserted through the bore 38 of neck 30. Second, upon depositing or removal of microorganisms, tissues, cells or other medium into and out of flask 10, any such material which may be inadvertently deposited on the inner wall 40 of neck 30 will have a tendency to slide back into the interior 28 of flask 10.

Figure 4:
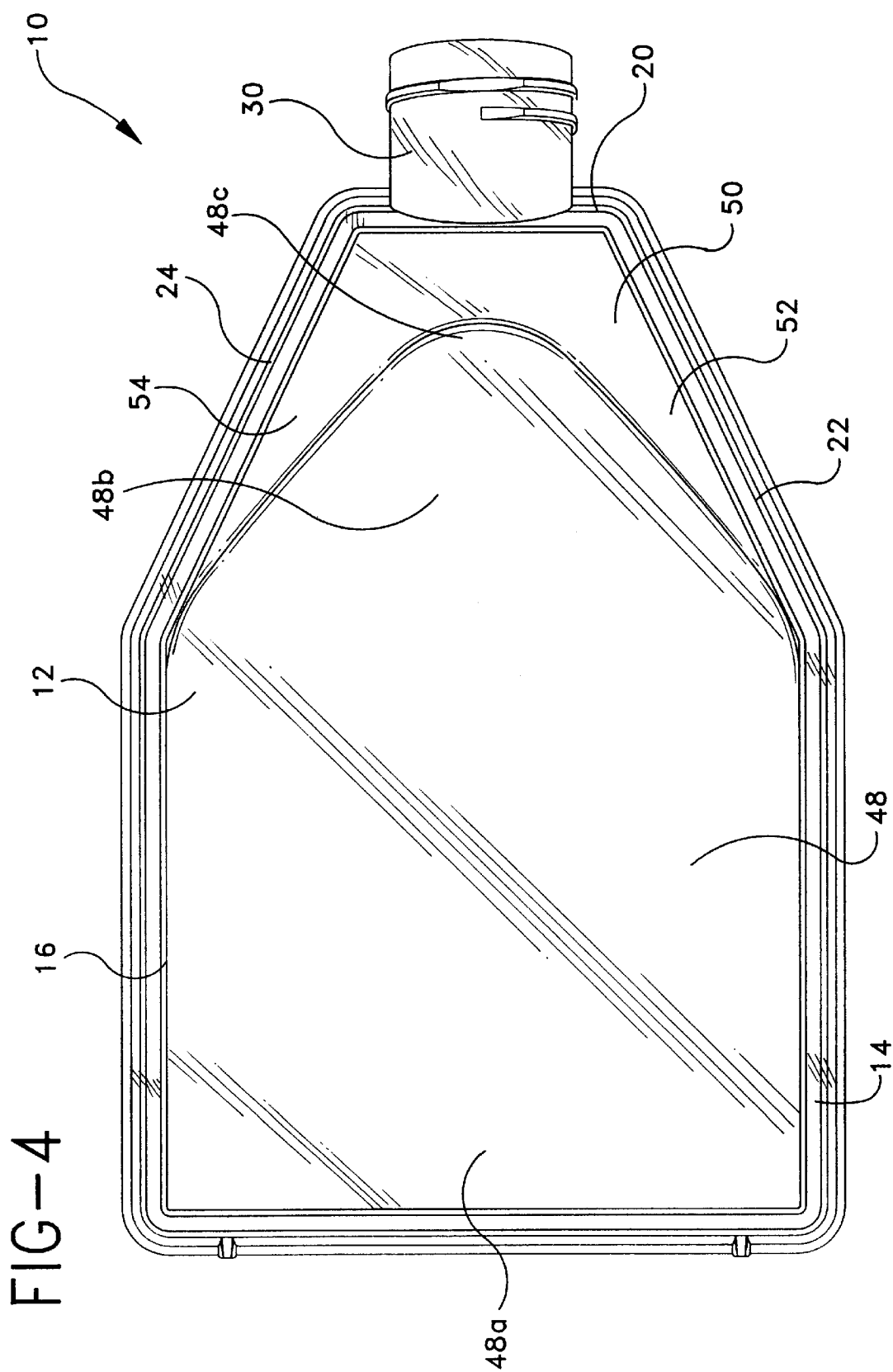
FIG. 4 is a bottom plan view of the tissue culture flask of FIG. 1.

As more fully illustrated with additional reference to FIG. 4, the bottom wall 12 of flask 10 includes a main planar portion 48 adjacent and between rear walls 16 and 18. Main planar portion 48 is generally flat and extends parallel to cover 26. Main planar portion 48 has a generally rectangular rear extent 48a and an arch-like forward extent 48b including a rounded crown 48c at the distal end thereof. Extending forwardly and upwardly from forward extension 48b is a ramp wall 50. Ramp wall 50 is generally a curved tapered surface, tapering from front wall 20 (FIG. 3) downwardly back towards main planar portion 48. Ramp wall portion 50 includes a pair of lateral ramp portions 52 and 54 positioned between forward extent 48b and each of forward transition walls 22 and 24 respectively. A front ramp portion 56 of ramp wall 50 extends between crown 48c and front wall 20. Ramp wall 50 generally has a shape, as shown in FIG. 1, which is generally curved in transverse section. Ramp wall 50 may have a conical, parabolic or other curved shape. Such a configuration assures that any tissues, microorganisms, medium or the like which may come in contact with ramp wall 50 adjacent neck 40 flows back into the main planar portion 48 of bottom wall 12.

As seen in FIG. 1, ramp wall 50 at the front end of bottom wall 12 has a rounded concave shape. The front end of flask 10 includes a depending multifaceted skirt 60 therearound. Skirt 60 depends to a level which is coplanar with bottom wall 12 so that, as shown in FIG. 1, flask 10 may lie flat. The skirt 60 serves to stabilize the flask in such a position.

Figure 5:
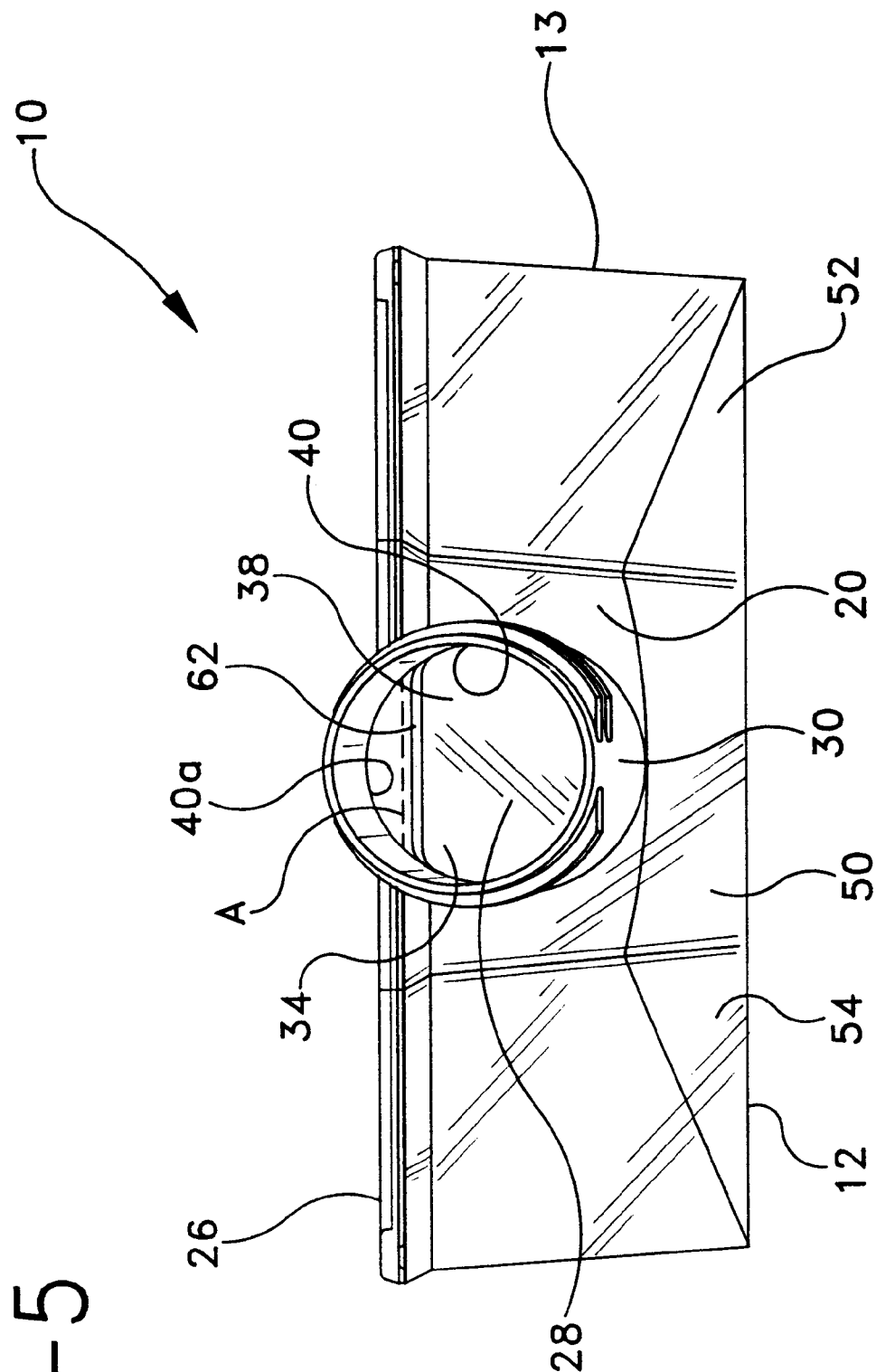
FIG. 5 is a front elevational showing of the tissue culture flask of FIG. 1.

With additional reference to FIG. 5, a further feature of the present invention is shown. Front wall 20 extends between ramp wall 50 and the upper extent of the side walls 13 bounding bottom wall 12. In order to increase pipette access to the entire interior 28 of flask 10, especially all portions of bottom wall 12, it is desirable to construct opening 34 in front wall 20 and accordingly, bore 38 in neck 30 to be as large as possible. This allows a pipette to be freely manipulated from the exterior of flask 10 with access being gained to the entire surface of bottom wall 12. In use, bottom wall 12, especially the rear main planar portion 48 thereof (FIG. 4), is the surface which accommodates the culture medium which supports the growth of the tissues. For periodic testing purposes, it may be necessary to remove samples of the tissue with a pipette or self scraper. Thus, access to all portions of the bottom wall is desirable.

The culture medium which supports the growth of the tissues typically covers the entire main planar portion 48 of bottom wall 12. The medium may be filled within flask 10 to such a level that it begins to rise along ramp wall 50. The theoretical limit to which the interior may be filled with culture medium and tissue is up to the bottom of opening 34. Any attempt to fill the flask further will result in material exiting opening 34 through neck 30. Thus, it can be appreciated that any attempts to overly enlarge opening 34 in front wall 20 so as to increase pipette accessibility to the interior 28 of flask 10 will result in a reduction of the usable medium-accommodating volume of flask 10. Raising the enlarged opening off the bottom wall would result in the necessity to increase the size of front wall 20 and thereby the stacked height of the flask. Attempts to reduce the opening 34 in front wall 30 in order to increase such usable volume results in limited access to the bottom wall 12.

The present invention provides for the arrangement of opening 34 and neck 30 on front wall 20 in such a position that the opening size may be maximized, thereby increasing accessibility, without unduly limiting the usable flask volume or increasing the stacked height. Opening 34 is provided on front wall 20 in such a position that an upper portion of the circle defining opening 34 extends above the upper extent of the side walls 13 of the flask. This is shown by dotted lines A in FIGS. 3 and 5. In order to close the gap that would otherwise exist between the upper portion 40a of inner cylindrical wall surface 40 and cover 26, the interior wall surface 40 includes a depending filler wall 62.

As shown in FIG. 3, filler wall 62 extends from the upper portion 40a of interior wall surface 40 of neck 30 adjacent front wall 20. The filler wall 62 enables the neck 30 to be raised slightly above the level of the upper extent of the side walls 13 so that the lower extent 30a of neck 30 is raised a sufficient distance above bottom wall 12 so as not to reduce the usable volume of the flask.

Figure 7:
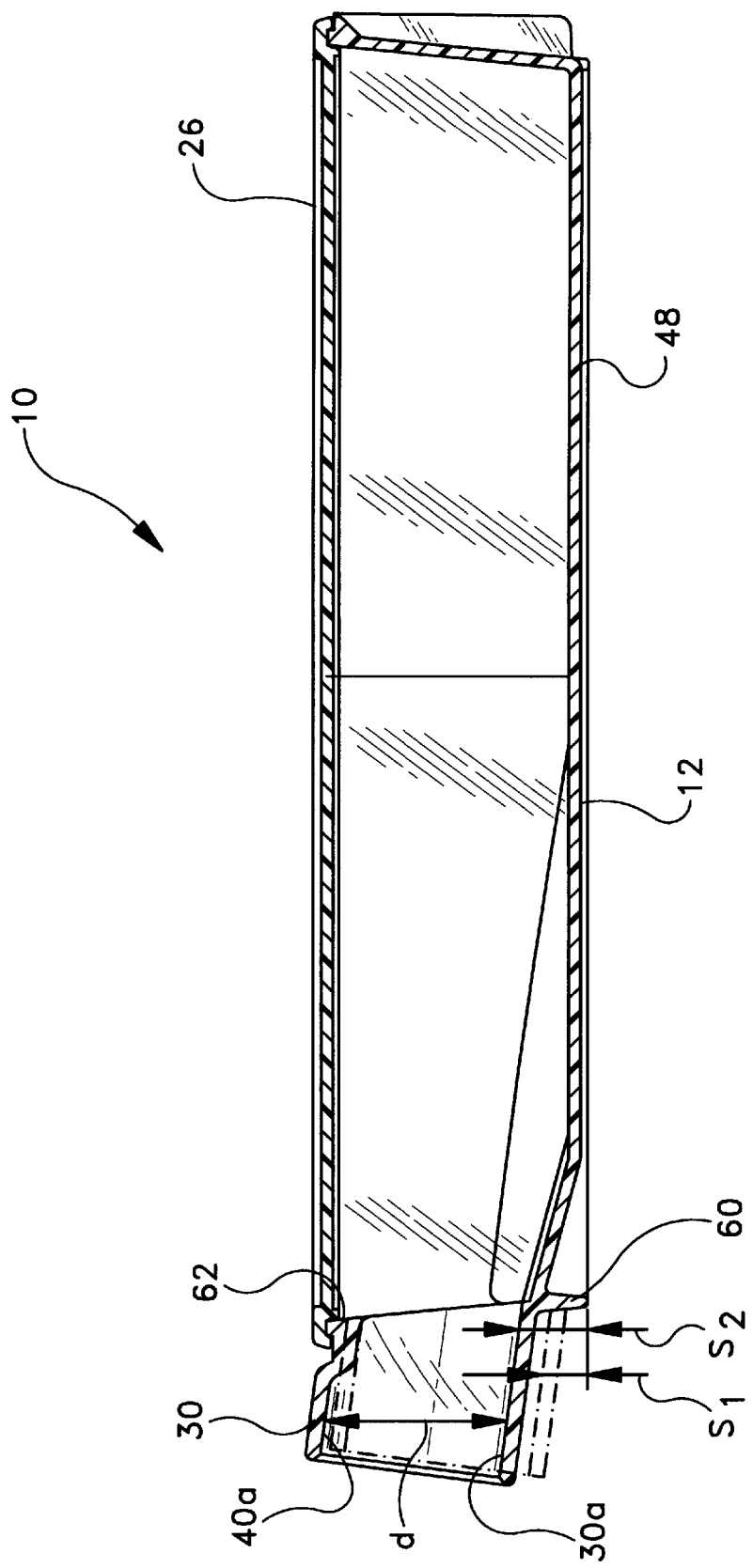
FIG. 7 is a sectional showing of the tissue culture flask of FIG. 3 with a schematic depiction of the position of the neck portion.

As shown in FIG. 7, neck 30 has an inner diameter of d. If the neck were to be positioned in a conventional fashion, extending from front wall 20 below the upper extent of the side walls 13 (as represented by dotted lines), the usable volume of flask 10 would be determined by the height $s_1$ between a lower extent 30a of the cylindrical wall of neck 30 and main planar portion 48 of bottom wall 12. By raising neck 30 above the upper extent of the side walls 13 and employing filler wall 62, the distance between the lower extent 30a of neck 30 and main planar portion 48 of bottom wall 12 is increased to $s_2$. This results in an increase in the usable volume of flask 10 without reducing the access opening thereinto.

Figure 6:
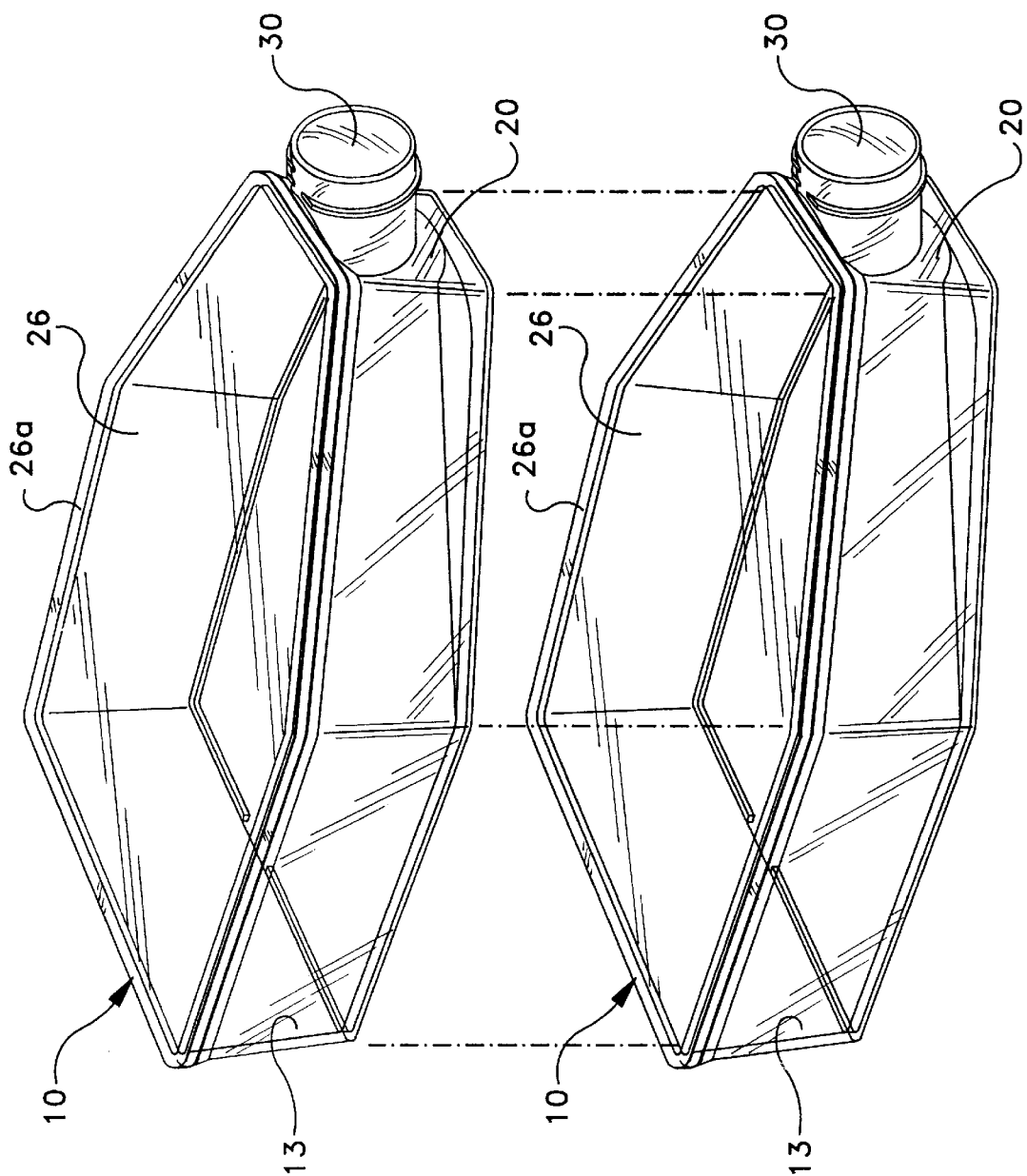
FIG. 6 is a perspective showing of a pair of tissue culture flasks of the type shown in FIG. 1, positioned in vertically stackable relationship.

Further, while the present invention permits increased access without reduction in usable volume, it also does so without increasing the stack height of flask 10. As shown in FIG. 6, plural flasks 10 are designed to be stackable one on top of another. Cover 26 may include a perimetrical raised lip 26a to accommodate the flask situated immediately thereabove. The stacked height of each flask 10 is dependent upon the height of the side walls 13 bounding bottom wall 12. The positioning of neck 30 with respect to front wall 20 enables the front wall height to be maintained at a minimal height expanse. Thus, the overall height of flask 10 is minimized. Also, as the neck is formed to be uniformly cylindrical, the stacked height of two or more flasks 10 is similarly minimized. By minimizing the stacked height of flasks 10, more flasks can be effectively accommodated in a given space within a chamber.

Figure 8:
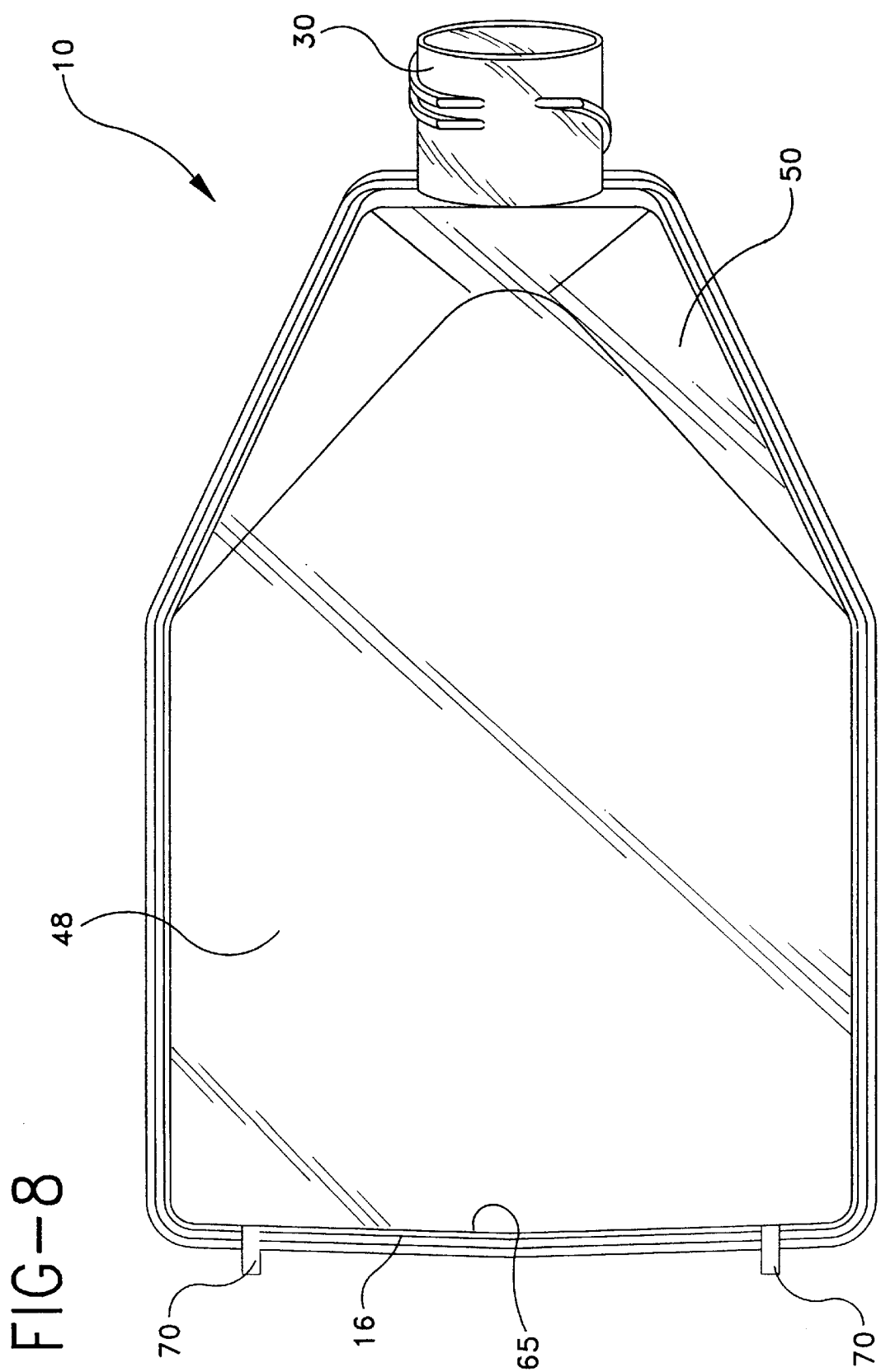
FIG. 8 is a bottom plan view of a further embodiment of the tissue culture flask of the present invention.

An additional feature of the present invention is shown in a further embodiment of FIG. 8. Rear wall 16 may be modified to have a central depression or trough 65 therein. Such a trough 65 provides a low point when flask 10 is stood upright on rear wall 16. To stabilize the flask in such a position, a pair of spaced apart feet 70 is provided (FIG. 2). When standing in such a position, the contents of flask 10 will have a tendency to accumulate in the trough 65. As the trough 65 is centrally located with respect to neck 30, direct pipette insertion to this low point is facilitated so that the entire contents of the flask may be emptied if desired.

Various changes to the foregoing described and shown structures would now be evident to those skilled in the art. Accordingly, the particularly disclosed scope of the invention is set forth in the following claims.

What is claimed is:

1. A laboratory flask comprising:
    a flask body having a generally flat bottom wall and upwardly extending front, back and lateral walls bounding said bottom wall and an upper, generally planar cover surface parallel to said bottom wall enclosing said flask body and defining a flask interior;
    said front wall including a generally circular opening therethrough providing access to said flask interior;
    an elongate hollow annular neck extending outwardly from said front wall opening and in communication therewith, said neck having uniform inner and outer cylindrical wall surfaces, a portion of the inner cylindrical wall surface of said annular neck being located at a position raised above a portion of said cover surface of said flask body;
    said neck further including a depending filler wall extending from the inner cylindrical wall surface thereof adjacent said front wall opening, said filler wall filling the gap which would otherwise exist between said inner cylindrical wall surface and said cover surface adjacent said front wall; and
    said bottom wall including a main planar portion back extent that is generally rectangular and an arch-like forward extent extending from the back extent, said arch-like forward extent having an arch cross section and a rounded crown.

\* \* \* \* \*